United States Patent

Gallenkamp

[11] 4,367,344

[45] Jan. 4, 1983

[54] PROCESS FOR THE PREPARATION OF 1-AMINO-CYCLOPROPANE-CARBOXYLIC ACID COMPOUNDS

[75] Inventor: Bernd Gallenkamp, Wuppertal, Fed. Rep. of Germany

[73] Assignee: Bayer Aktiengesellschaft, Leverkusen, Fed. Rep. of Germany

[21] Appl. No.: 180,557

[22] Filed: Aug. 22, 1980

[30] Foreign Application Priority Data

Sep. 6, 1979 [DE] Fed. Rep. of Germany ....... 2936038

[51] Int. Cl.³ .................. C07C 101/18; C07C 125/06; C07C 101/14
[52] U.S. Cl. ...................................... 560/115; 71/106; 71/111; 71/113; 260/459 R; 560/48; 560/124; 562/506; 562/457
[58] Field of Search .................. 560/115, 124, 48; 562/457, 506

[56] References Cited

U.S. PATENT DOCUMENTS 3,445,499 5/1969 Martel .
4,083,863 4/1978 Brand .

FOREIGN PATENT DOCUMENTS 1047267 5/1964 United Kingdom .

OTHER PUBLICATIONS

Rich, Synthesis, p. 46, (1978).

*Primary Examiner*—Michael L. Shippen
*Attorney, Agent, or Firm*—Felfe & Lynch

[57] ABSTRACT

A process for the preparation of 1-amino-cyclopropane-carboxylic acid or a derivative thereof of the general formula

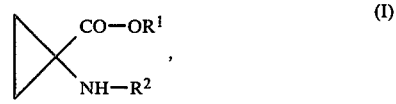

in which
$R^1$ represents hydrogen or alkyl and
$R^2$ represents hydrogen or a radical $-CO-R^3$, wherein
$R^3$ represents hydrogen, alkyl, aryl or alkoxy, in which a 2-cycloamino-4-methylthio-butanoic acid ester ("acyl-methionine ester") of the general formula

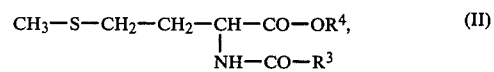

in which
$R^3$ has the meaning indicated above and
$R^4$ represents alkyl, is reacted successively with dimethyl sulphate and an alkali metal alcoholate, if appropriate in the presence of a diluent, at a temperature between 80° C. and 150° C., the product is then optionally saponified with aqueous alkali metal hydroxide or alkaline-earth metal hydroxide at a temperature between 70° C. and 150° C., the reaction mixture thereby obtained is acidified with concentrated hydrochloric acid at a temperature between 0° C. and 30° C., and the hydrochloride formed is then treated, in methanolic solution, with propylene oxide at a temperature between −5° C. and +20° C.

10 Claims, No Drawings

PROCESS FOR THE PREPARATION OF 1-AMINO-CYCLOPROPANE-CARBOXYLIC ACID COMPOUNDS

This invention relates to a process for the preparation of 1-amino-cyclopropane-carboxylic acid compounds, including said acid and derivatives thereof.

It is known that 1-amino-cyclopropane-carboxylic acid is obtained when α-acylamino-acrylic acid esters are reacted with diazomethane, the pyrazolines thereby formed are pyrolized and the resulting 1-acylamino-cyclopropane-carboxylic acid esters are saponified (see Monatshefte für Chemie (Vienna) 103 (1972), 288–291).

However, there are great risks involved in the use of diazomethane because it is toxic and explosive.

It is furthermore known that 1-amino-cyclopropane-carboxylic acid esters can be prepared by hydrolysis of 1-isocyano-cyclopropane-carboxylic acid esters, which are obtained from isocyano-acetic acid esters and 1,2-dibromoethane in the presence of strong bases, for example sodium hydride (see Liebigs Ann. Chem. 1973, 611–618). However, the carcinogenic nature of 1,2-dibromo-ethane demonstrated in animal experiments precludes the use of this compound.

It has furthermore been disclosed that 1-amino-cyclopropane-carboxylic acid is obtained when N-butoxycarbonyl-methionine methyl ester is S-alkylated with fluorosulphonic acid methyl ester and the product is then cyclized with sodium hydride to give 1-butoxycarbonyl-amino-cyclopropane-carboxylic acid methyl ester, which is then saponified (see Synthesis 1978, 46). However, fluorosulphonic acid methyl ester and sodium hydride are not very suitable starting materials for industrial requirements.

The present invention now provides a process for the preparation of 1-amino-cyclopropane-carboxylic acid or a derivative thereof, of the general formula $$\triangleright\!\!\!<\!\!\!\begin{array}{l}CO-OR^1\\NH-R^2\end{array} \quad (I)$$

in which
R$^1$ represents hydrogen or alkyl and
R$^2$ represents hydrogen or a radical —CO—R$^3$, wherein
R$^3$ represents hydrogen, alkyl, aryl or alkoxy, in which a 2-acylamino-4-methylthio-butanoic acid ester ("acyl-methionine ester") of the general formula $$CH_3-S-CH_2-CH_2-\underset{\underset{NH-CO-R^3}{|}}{CH}-CO-OR^4, \quad (II)$$

in which
R$^3$ has the meaning indicated above and
R$^4$ represents alkyl,
is reacted successively with dimethyl sulphate and an alkali metal alcoholate, if appropriate in the presence of a diluent, at a temperature between 80° C. and 150° C., the product is then optionally saponified with aqueous alkali metal hydroxide or alkaline-earth metal hydroxide at a temperature between 70° C. and 150° C., the reaction mixture thereby obtained is acidified with concentrated hydrochloric acid at a temperature between 0° C. and 30° C., and the hydrochloride formed is then treated, in methanolic solution, with propylene oxide at a temperature between −5° C. and +20° C.

The formula (II) includes the various possible stereoisomers (optical isomers) and mixtures thereof (racemates).

It is to be described as exceptionally surprising that 1-amino-cyclopropanecarboxylic acid and derivatives thereof of the formula (I) can be prepared in a very high yield by the process according to the invention, since on the basis of the known state of the art, it had to be reckoned that no cyclization would occur when basic alkali metal alcoholates, which are substantially weaker compared with alkali metal hydrides, are used.

The process according to the invention has a number of advantages. Thus, the substances required as starting materials are accessible in a simple manner, even in relatively large amounts, and can also be handled on an industrial scale without problems. Furthermore, the expenditure on apparatus necessary for carrying out the process according to the invention is low, and working up of the reaction mixture obtained when the reaction has ended presents no difficulties. The process according to the invention thus represents a valuable enrichment of the art.

If, for example, 2-acetamino-4-methylthio-butanoic acid ethyl ester ("acetylmethionine ethyl ester"), dimethyl sulphate and potassium ethylate are used as starting substances, the course of the reactions in the process according to the invention can be outlined by the following equation:

$$CH_3-S-CH_2-CH_2-\underset{\underset{NH-CO-CH_3}{|}}{CH}-CO-OC_2H_5 \xrightarrow{+(CH_3O)_2SO_2}$$

$$\underset{CH_3}{\overset{CH_3}{\diagdown}}\!\!\overset{\oplus}{S}\!-CH_2-CH_2-\underset{\underset{NH-CO-CH_3}{|}}{CH}-CO-OC_2H_5 \xrightarrow[\substack{-HOC_2H_5\\-CH_3SCH_3\\-CH_3OSO_3K}]{+KOC_2H_5}$$

$$CH_3O-SO_3^{\ominus}$$

$$\triangleright\!\!\!<\!\!\!\begin{array}{l}CO-OC_2H_5\\NH-CO-CH_3\end{array}$$

Formula (II) provides a definition of the 2-acylamino-4-methylthio-butanoic acid esters to be used as starting substances. Preferably, in this formula,
R$^3$ represents acetyl and
R$^4$ represents alkyl with 1 to 4 carbon atoms.

Examples of the compounds (II) which may be mentioned are 2-acetamino-4-methylthio-butanoic acid methyl ester, ethyl ester, n-propyl ester, iso-propyl ester, n-butyl ester, iso-butyl ester, sec.-butyl ester and tert.-butyl ester.

The 2-acylamino-4-methylthio-butanoic acid esters of the formula (II) are already known, or they can be prepared in a simple manner by processes which are known in principle (see U.S. Pat. No. 3,963,573).

Preferred alkali metal alcoholates, which are also required as starting substances in carrying out the process according to the invention, are the sodium or potassium salts of alcohols with 1 to 4 carbon atoms. Sodium methylate, ethylate, n- and iso-propylate and n-, iso-, sec.- and tert.-butylate and potassium methylate, ethylate, n- and iso-propylate and n-, iso-, sec.- and tert.-butylate may be mentioned in particular.

Preferred diluents for the reaction according to the invention are polar organic solvents. These include, as preferences, alcohols, for example methanol, ethanol, n- and iso-propanol and n-, iso-, sec.- and tert.-butanol, and also aprotic solvents, for example dimethylformamide, dimethylsulphoxide and tetrahydrofuran.

Sodium hydroxide, potassium hydroxide and calcium hydroxide, in particular, may be mentioned as alkali metal hydroxides and as alkaline-earth metal hydroxides which are used for the saponification of the compounds obtained in the process according to the invention.

The reaction temperatures can be varied within a substantial range in carrying out the process according to the invention. In general, the reaction is carried out at a temperature between 80° C. and 150° C., preferably between 90° C. and 120° C. The reaction temperatures can also be varied within a substantial range in the saponification optionally to be carried out. In general, the saponification is carried out at a temperature between 70° C. and 150° C., preferably between 80° C. and 120° C. The reaction temperatures can be varied within a certain range for the conversion of the saponification products into the corresponding hydrochlorides and for the subsequent treatment with propylene oxide. In general, the preparation of the hydrochlorides is carried out at a temperature between 0° C. and 30° C., preferably between 5° C. and 20° C. The treatment with propylene oxide is in general carried out at a temperature between −5° C. and +20° C., preferably between 0° C. and 10° C.

The process according to the invention is in general carried out under normal pressure. However, it is also possible to carry it out under a pressure matching the vapor pressure, at the reaction temperature, of the diluent used.

In carrying out the process according to the invention, 1 to 2 moles, preferably 1.1 to 1.5 moles, of dimethyl sulphate and 1 to 2 moles, preferably 1.1 to 1.5 moles, of alkali metal alcoholate are employed per 1 mole of 2-acylamino-4-methylthio-butanoic acid ester of the formula (II).

The reaction products are isolated by customary methods. In general, a procedure is followed in which an organic solvent which is sparingly soluble in water is added to the reaction mixture after cooling, and the organic phase is separated off, washed with water and, after drying, is concentrated, after which the reaction product remains as an oily residue or as a crystalline substance.

In a preferred embodiment of the process according to the invention, the starting compounds of the formula (II) are initially introduced, if appropriate in the form of melts, and dimethyl sulphate is added dropwise. A solution of an alkali metal alcoholate in one of the abovementioned solvents is then added dropwise and the reaction mixture is stirred at the required temperature, if appropriate under reflux of the solvent, for a relatively long time. It is then worked up in the manner indicated above.

If the 1-acylamino-cyclopropane-carboxylic acid esters obtained in the process according to the invention are to be saponified, this is effected by first saponifying the particular product with an excess of aqueous alkali metal hydroxide or alkaline-earth metal hydroxide. The reaction mixture is then acidified with concentrated aqueous hydrochloric acid, while cooling, and is evaporated to dryness. The product which remains is taken up in methanol or ethanol and the undissolved constituents are filtered off. The filtrate is then concentrated to dryness, after which the hydrochloride of 1-amino-cyclopropanecarboxylic acid remains. If the latter is to be converted into the free 1-amino-cyclopropanecarboxylic acid, it is taken up in methanol, and propylene oxide is added. 1-Amino-cyclopropanecarboxylic acid is thereby obtained as a crystalline product which can be filtered off.

The 1-amino-cyclopropanecarboxylic acid hydrochloride does not have to be isolated. Rather, it is also possible to obtain 1-amino-cyclopropanecarboxylic acid by adding propylene oxide directly to a methanolic solution of 1-amino-cyclopropanecarboxylic acid hydrochloride.

The active compounds which can be prepared according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds, at verges, at airports or in fruit orchards. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging. Use of growth regulators for shortening and strengthening the stem enables higher amounts of fertilizer to be applied to increase the yield, without danger of the cereal lodging.

In the case of many crop plants, inhibition of the vegetative growth permits denser planting of the crop, so that a greater yield per area of ground can be achieved. An advantage of the smaller plants thus produced is also that the crop can be worked and harvested more easily.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great-utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting.

Using growth regulators it is also possible favorably to influence the production or the efflux of secondary plant materials. The stimulation of latex flow in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants and also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dye-stuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming and coating. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The amounts applied can be varied within a substantial range. In general, 0.01 to 50 kg, preferably 0.05 to 10 kg, of the active compound are employed per hectare of soil surface.

The present invention also provides a plant-growth regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Example.

In this Example, the compounds according to the present invention are each identified by the number (given in brackets) of the corresponding preparative Example, which will be found later in this specification.

EXAMPLE A

Stimulation of ethylene biosynthesis

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Pieces of leaf of identical size were punched from soya bean leaves. A constant number of pieces of leaf was incubated for 1 hour in Petri dishes which were filled with 10 ml of the active compound preparations or with corresponding control solutions without active compounds. Thereafter, the pieces of leaf were introduced into vessels which were closed air-tight, together with 1 ml of the particular preparation of active compound or control solution. After 24 hours the ethylene which had collected in the vessels was determined by customary methods of detection. The evolution of ethylene from the pieces of leaf treated with the preparation of active compound was compared with the evolution of ethylene of the controls.

In the table which follows:

0 denotes no action

+ denotes slight stimulation of ethylene biosynthesis

++ denotes moderate stimulation of ethylene biosynthesis

+++ denotes high stimulation of ethylene biosynthesis

This test was particularly suitable for illustrating the growth-regulating properties of the compounds according to the invention.

The plant hormone ethylene affects numerous processes during the development of the plants. An increase in ethylene biosynthesis, such as can be achieved with the substances according to the invention, makes it possible to control these processes. The following may be mentioned here as examples in which there is a particular commercial interest: detachment of fruit, acceleration of ripening of fruit and leaves, induction of flowering, germination of seeds, thinning-out of fruit, stimulation of latex flux, for example in Hevea, influencing of gender and inhibition of growth, for example also to prevent the lodging of cereals.

The active compounds and the results can be seen from the Table which follows.

TABLE A

| Active compound | Stimulation of ethylene biosynthesis Active compound concentration in % | Action |
|---|---|---|
| (1) | 0.001 | +++ |
| (2) | 0.001 | +++ |
| — (control) | — | 0 |

PREPARATIVE EXAMPLES

EXAMPLE 1

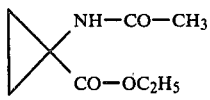  (1)

16.4 g (0.13 mol) of dimethyl sulphate were very slowly added dropwise to 20.5 g (0.1 mol) of molten DL-N-acetylmethionine methyl ester at 110° C. When the addition had ended, the mixture was subsequently stirred for a further 5 minutes. A sodium ethylate solution prepared from 50 ml of ethanol and 2.76 (0.12 mol) of sodium was then added dropwise and the mixture was heated under reflux for 25 hours. Thereafter, it was filtered and the filtrate was concentrated. The residue was taken up in 150 ml of chloroform and washed with 50 ml of water. The organic phase was separated off, dried with sodium sulphate and concentrated. After incipient distillation of the residue, 16 g (93.5% of theory) of an oil which, according to analysis by gas chromatography, consisted of 1-N-acetyl-aminocyclopropane-1-carboxylic acid ethyl ester to the extent of 80%, remained.

EXAMPLE 2

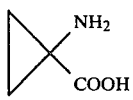  (2)

(a) A mixture of 17.1 g (0.1 mol) of 1-N-acetyl-cyclopropane-1-carboxylic acid ethyl ester, 19.6 g (0.35 mol) of calcium hydroxide and 60 ml of water was heated under reflux for 12 hours. After cooling, the reaction mixture was acidified with concentrated hydrochloric acid, while cooling with ice, and evaporated to dryness. The residue was taken up in ethanol, the insoluble constituents were filtered off and the solvent was stripped off from the filtrate under reduced pressure. After drying the residue, 13.5 g (98% of theory) of 1-aminocyclopropane-1-carboxylic acid hydrochloride remained.

(b) 8.7 g (0.15 mol) of propylene oxide were added dropwise to a solution of 13.8 g (0.1 mol) of 1-aminocyclopropane-1-carboxylic acid hydrochloride in 20 ml of methanol, while cooling with ice and stirring intensively. After a few minutes, the free 1-aminocyclopropane-1-carboxylic acid started to crystallize out. The reaction mixture was left to stand overnight at temperatures between 0° C. and 4° C. in order to bring the crystallization to completion. After filtering off the product and drying it, 9.6 g (95% of theory) of 1-aminocyclopropane-1-carboxylic acid were obtained.

It will be understood that the specification and examples are illustrative, but not limitative of the present invention and that other embodiments within the spirit and scope of the invention will suggest themselves to those skilled in the art.

What is claimed is:

1. Process for the preparation of a 1-amino-cyclopropane-carboxylic acid compound of the formula

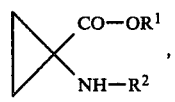  (I)

wherein
$R^1$ is alkyl;
$R^2$ is a radical —CO—$R^3$ wherein
$R^3$ is hydrogen, alkyl, aryl or alkoxy, which process comprises reacting a 2-acylamino-4-methylthiobutanoic acid ester compound of the formula

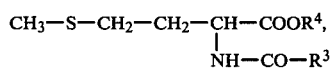  (II)

in which
$R^3$ is as identified above and
$R^4$ is alkyl, successively with dimethylsulfate and an alkali metal alcoholate at a temperature from 80° to 150° C.

2. Process as claimed in claim 1 wherein said successive reaction with dimethylsulfate and an alkali metal alcoholate is carried out in the presence of a diluent.

3. Process as claimed in claim 1 wherein the reaction of the compound II is carried out at a temperature between 90° and 120° C.

4. Process as claimed in claim 1 wherein 1 to 2 moles of dimethylsulfate and 1 to 2 moles of alkali metal alcoholate are used per mole of compound II.

5. Process as claimed in claim 1 wherein a sodium or potassium salt of an alcohol with 1 to 4 carbon atoms is used as the alkali metal alcoholate.

6. Process as claimed in claim 2 wherein the reaction of the compound II is effected in a polar organic solvent.

7. Process as claimed in claim 1 wherein $R^3$ is acetyl.

8. Process as claimed in claim 1 wherein $R^4$ is alkyl with 1 to 4 carbon atoms.

9. Process as claimed in claim 1 wherein D,L-N-acetyl-methionine methyl ester is used as compound II.

10. Process for the preparation of a 1-amino-cyclopropane-carboxylic acid compound of the formula

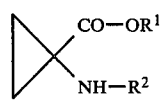  (I)

wherein
$R^1$ is hydrogen;
$R^2$ is hydrogen
which process comprises reacting D,L-N-acetylmethionine methyl ester successively with dimethylsulfate and sodium methylate; at a temperature from 80° to 150° C. the product obtained is subsequently saponified with aqueous calcium hydroxide, the mixture is then acidified with concentrated hydrochloric acid and the hydrochloride formed is treated, in methanolic solution, with propylene oxide.

* * * * *